United States Patent [19]

Hillenkamp et al.

[11] 4,243,887

[45] Jan. 6, 1981

[54] PROCESS AND APPARATUS FOR ANALYZING A SAMPLE WITH THE AID OF PULSED LASER IRRADIATION

[75] Inventors: Franz Hillenkamp, Frankfurt; Raimund Kaufmann, Düsseldorf; Eberhard Unsöld, Oberschleissheim; Rainer Nietsche, Frankfurt; Reiner Wechsung, Cologne; Henning Vogt, Cologne; Walter Bank, Cologne ln; Lothar Aberle, Sindorf, all of Fed. Rep. of Germany

[73] Assignee: Leybold-Heraeus GmbH, Cologne, Fed. Rep. of Germany

[21] Appl. No.: 35,089

[22] Filed: May 1, 1979

[30] Foreign Application Priority Data

May 5, 1978 [DE] Fed. Rep. of Germany ....... 2819711

[51] Int. Cl.³ ............................................. H01J 27/00
[52] U.S. Cl. ................................. 250/423 P; 250/425
[58] Field of Search ................. 250/423 P, 425, 281; 204/DIG. 11, 298, 192; 219/121 L; 47/53, 42

[56] References Cited

U.S. PATENT DOCUMENTS

| 2,621,296 | 12/1952 | Thompson | 250/425 |
|---|---|---|---|
| 3,294,970 | 12/1966 | Jenckel | 250/423 P |
| 3,955,090 | 5/1976 | Astley | 250/423 P |
| 4,000,423 | 12/1976 | Janes | 250/423 P |

Primary Examiner—Harold A. Dixon
Attorney, Agent, or Firm—Spencer & Kaye

[57] ABSTRACT

A method and apparatus for analyzing a sample comprising the steps of irradiating a selected area of the sample with a first burst of laser energy to vaporize the sample, condensing the vaporized sample on the surface of an intermediate carrier and analyzing the condensed sample material deposited on the intermediate carrier.

16 Claims, 7 Drawing Figures

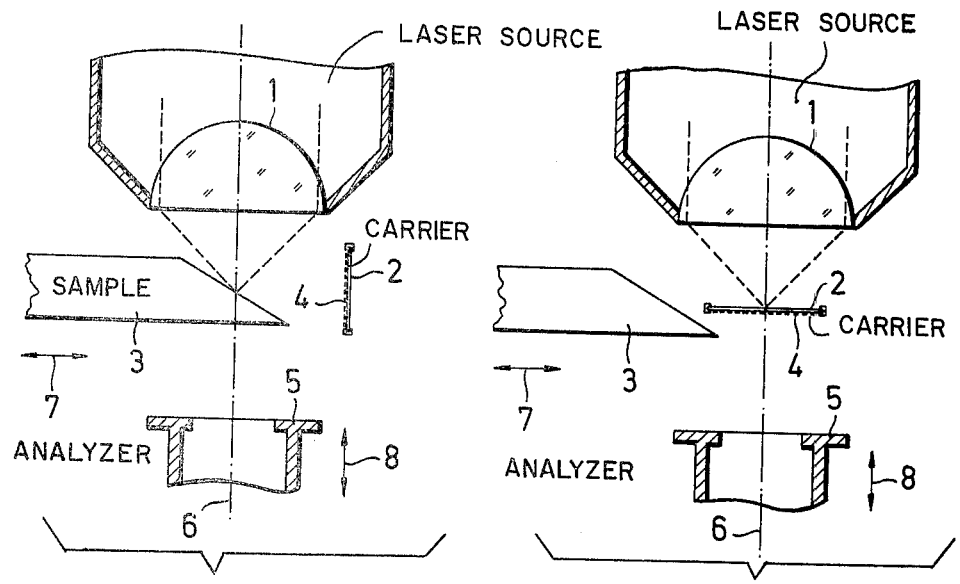
FIG. 1a
FIG. 1b
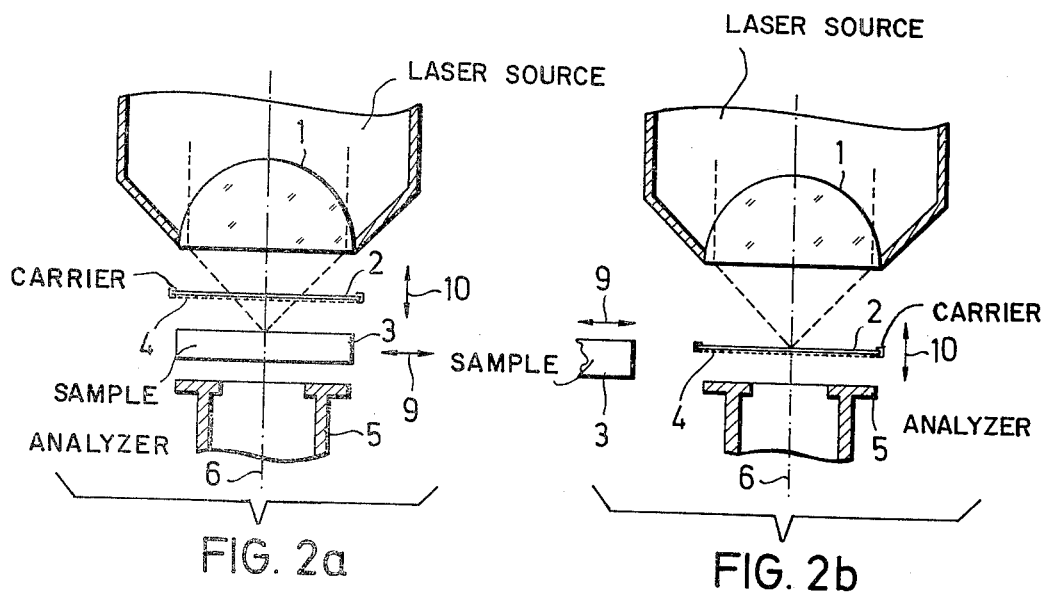
FIG. 2a
FIG. 2b

PROCESS AND APPARATUS FOR ANALYZING A SAMPLE WITH THE AID OF PULSED LASER IRRADIATION

BACKGROUND OF THE INVENTION

This invention relates to a process and apparatus for analyzing a sample of a material of unknown composition. In particular, the invention relates to the preparation of a sample for analysis by irradiating it with energy emitted by a pulsed laser beam.

German Offenlegungsschrift No. 1,598,632 discloses a process wherein a sample to be analyzed is exposed to electromagnetic radiation, especially coherent radiation, thereby producing vapors, plasmas, ion beams, and the like. These products are then subjected to emission or absorption spectroscopic analysis and/or mass spectroscopy. In carrying out this process, the laser light is focused by means of a collecting lens onto that portion of the surface area of the sample which faces the analyzing means.

A prerequisite for such an arrangement is that the sample material be essentially transparent to the light emitted by the laser. If the sample is not transparent to laser light, it must be so thin that the laser burst will produce a hole in the sample. Then, the sample particles to be analyzed can pass through the sample to the side facing away from the collecting lens where the analyzing device is located.

One disadvantage of the prior art arrangement is that not every sample can be fabricated as a thin film. Such a sample can be viewed only in incident light while aiming the laser beam; thus, the side of the sample facing the analyzer is not visible. Consequently, data indicating which part of a sample, which frequently has a specific structure, has been excited by the laser beam and vaporized are fraught with uncertainties.

Arrangements are also known wherein nontransparent samples are irradiated with a laser beam in the presence of incident light, and the thus-produced ions transferred directly by suction into a mass analyzer. This method has the disadvantage that the collecting lens system focusing the laser light onto the sample, as well as the inlet opening of the mass analyzer (or of an ion optical system connected in front of the mass analyzer), must be on the same side of the sample. Since both devices occupy a large amount of space, the collecting lens systems and inlet opening are at a relatively great distance from the location on the sample at which the laser beam impinges. As a consequence, it is impossible to direct the laser beam to particularly small zones of the sample, although this is desirable in laser microscopy wherein the irradiated zone can be reduced as the sample is brought closer to the collecting lens system. Further, a relatively large spacing between the sample and the analyzing device results in poor acceptance of the emitted ions.

SUMMARY OF THE INVENTION

An object of the present invention is to provide a method and apparatus for effecting a controlled analysis of an extremely small area of a sample which exhibits low transparency, or no transparency at all, to laser light.

This object is attained by vaporizing the selected area of the sample with a burst of laser energy, condensing the vapor-phase sample material on the surface of an intermediate carrier; and then analyzing the sample layer disposed on the intermediate carrier. Several analytical methods can be utilized for analyzing the vaporized sample layer. These include surface analysis, as electron spectroscopy or secondary ion mass spectrometry and optical methods.

In carrying out the invention, it is particularly advantageous to vaporize the sample material by a first laser burst and then provide conditions for the analysis of the sample layer by a second laser burst. This process makes it possible to extract a very small portion of the sample of interest with the first laser burst. Furthermore, the sample is extracted with an optimally close distance between the sample and the collecting lens system, in incident light and with high precision.

The intermediate carrier is made relatively small and thin so that it does not interfere with the selection of the distance between the sample and the collecting lens system. It is important that only the material vaporized from the area of the sample on which the first laser burst impinges be transferred to the intermediate carrier. Thereafter, a second laser burst is fired onto the sample material which has been vapor-deposited on the intermediate carrier and the analysis carried out. During this second laser burst, optimum conditions can be established for mass analysis, when this is the analytical method chosen.

The intermediate carrier may be formed of a material transparent to laser light. This makes it possible to bring the surface of the intermediate carrier on which the condensed sample material has been deposited face-to-face with the analyzer. It is furthermore advantageous to analyze, by means of the second laser burst, either an exactly defined portion or the entire sample vaporized by means of the first burst. In this way, quantitative analyses are made possible.

In another embodiment of the invention, the intermediate carrier having the vapor-deposited sample thereon is subjected to repeated laser bursts. The thus-obtained spectra, which may be light-optical or mass-spectrometric spectra, can be added until the required statistic accuracy has been obtained. Also, during the second burst, the laser beam may be focused so that a small portion of the intermediate carrier is vaporized in addition to the sample. The material of the intermediate carrier can then be used for calibrating purposes during the analysis. The material serving the calibrating purposes can also be applied beforehand to the intermediate carrier, for example, by vapor deposition.

BRIEF DESCRIPTION OF THE DRAWINGS

Additional advantages and details will be described with reference to the embodiments, illustrated schematically in the drawings wherein:

FIGS. 1a and 1b are schematic diagrams showing a first arrangement of the apparatus for carrying out the vaporizing and analyzing steps of the method, respectively.

FIGS. 2a and 2b are schematic diagrams showing a second arrangement of the apparatus for carrying out the vaporizing and analyzing steps of the method, respectively.

DESCRIPTION OF THE PREFERRED EMBODIMENTS

In all of the figures, the collecting lens system for focusing the laser light is denoted by 1, the intermediate carrier by 2, the sample by 3, the sample layer condensed on the intermediate carrier 2 by the dashed lines 4 and a recording unit, such as an ion optical system for receiving the ions produced during the second laser burst, by the numeral 5.

The pulsed laser may be of any suitable type, a preferred device being a ruby laser or Neodym YAG-Laser with Q-switch.

The analysis may be conducted with conventional instrumentation such as quadruple mass spectrometer or time-of-flight mass spectrometer.

If, in place of mass analysis, another analytical method is employed, the ion optical system 5 would be replaced by a corresponding measurement unit such as an optical prism or diffraction grating or monochromate.

Figures 3A, 3B:
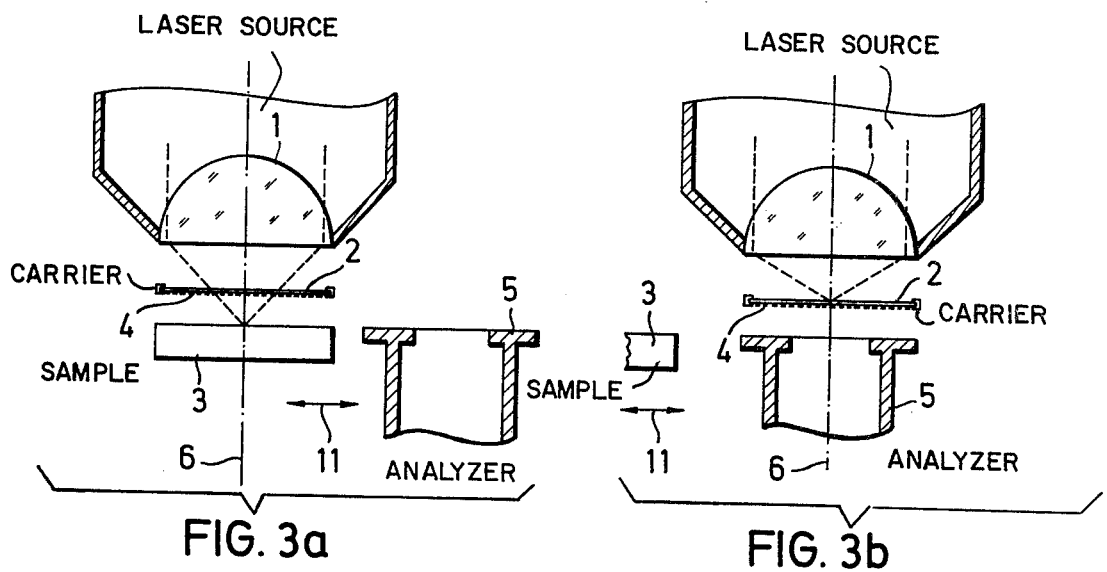
FIGS. 3a and 3b are schematic diagrams showing a third arrangement of the apparatus for carrying out the vaporizing and analyzing steps of the method, respectively.

FIGS. 1a, 2a and 3a each show the position of the individual elements with respect to one another during the first laser burst and FIGS. 1b, 2b and 3b show the arrangement during the second laser burst. The axis of each system is denoted by the numeral 6.

In the embodiment of FIGS. 1a and 1b, the laser beam is focused onto the surface of the sample 3, which is displaceable in a direction approximately perpendicular to the axis 6 as shown by the arrow 7. The vapor produced by irradiating the sample 3 with a burst of laser energy is condensed in the form of a sample layer 4 on the intermediate carrier 2 disposed beside the sample. To bring the sample 3 as close as possible to the lens system 1 prior to the first burst of laser energy, the ion optical system 5 is made displaceable in a direction approximately parallel to the axis 6 as shown by the arrow 8. Before the second burst of laser energy, the sample 3 is removed from the zone of the laser beam so that intermediate carrier 2 can be placed at that location and so that the sample layer 4 condensed thereon faces the ion optical system 5. The optical system 5 is moved toward the intermediate carrier 2 to improve acceptance.

Thereafter, the sample layer 4 is subjected to a second laser burst and the vaporized product analyzed by means of the system 5.

In some cases, the intermediate carrier 2 is also vaporized to provide calibration. More specifically, an epoxy resin with known amounts of dopants with concentration in the range of 7 ppm to 7000 ppm is used to measure the peak heights for the doped isotopes.

In the embodiments of FIGS. 2a and 2b, during the first laser burst, the intermediate carrier 2 is disposed between the collecting lens system 1 and the sample 3. A prerequisite for this is that the material forming the intermediate carrier 2 be transparent to laser light and may consist, for example, of a thin film or a sheet of glass. After the first laser burst, the sample 3 is shifted in the direction of arrow 9 approximately perpendicular to the axis 6 and the intermediate carrier 2 is displaced in the direction of arrow 10 approximately parallel to the axis 6, as shown in FIG. 2b. The second laser burst is then triggered to permit analysis of the sample layer 4.

In the embodiment of FIGS. 3a and 3b, the sample and the ion optical system 5 are displaceable together in the direction of arrow 11 perpendicular to the axis 6. During the first burst (FIG. 3a), the intermediate carrier 2 is disposed between the collecting lens system 1 and the sample 3. Thereafter, the sample and the ion optical system are shifted into the position shown in FIG. 3b. In addition, in this embodiment, the focusing of the laser beam onto the sample layer 4 must be changed since the distance between the intermediate carrier 2 and the collecting lens system remains unchanged. Then, the second laser burst is triggered and the sample layer 4 analyzed.

Figure 4:
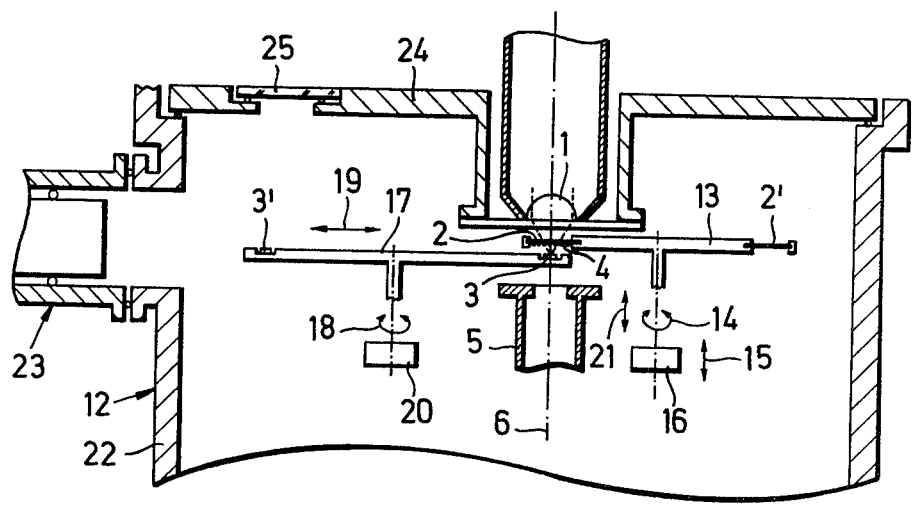
FIG. 4 illustrates additional details of an apparatus in accordance with the invention.

In FIG. 4, a portion of the evacuatable housing 12 is illustrated. The housing 12 encloses a carrier support 13 which holds several intermediate carriers 2, 2' about its periphery. Support 13 is rotatable in the direction of arrow 14 with its axis of rotation parallel to the axis 6. The carrier support 13 may also be displaced in its entirety in the direction of arrow 15 parallel to the axis 6 so that either intermediate carrier 2 or 2' is located in the zone of the lens system 1. The mechanism for rotating and translating the carrier suppot 13 is indicated by the block 16.

A sample support 17 is located in the housing 12 and is rotatable in the direction of arrow 18 with its axis also parallel to the axis 6. Support 17 is displaceable in the direction of arrow 19 perpendicular to the axis 6. The mechanism for rotating and displacing sample support 17 is denoted by block 20. Along its periphery, the sample support 17 is provided with holders, not indicated in detail, for several samples 3 and 3', respectively which can be selectively brought into close proximity with the lens system 1. Further, the sample support 17 can be provided with cooling means if desired.

During the first laser burst, the individual elements are in the position shown in FIG. 4 so that the laser beam strikes the sample 3 and vapor is condensed on the intermediate carrier 2 as a layer 4. Thereafter, the sample 3 is removed from the area immediately surrounding the axis 6 by shifting the sample support 17 perpendicular to the axis 6 in the direction of arrow 19.

Such shifting is unnecessary if the support 17 has sector-like cutouts, not shown. If the cutouts are provided, the support 17 may be rotated in such a way that the cutout exposes the path between the intermediate carrier 2 and the ion optical system 5. Thereafter, the laser beam is focused on the layer 4 by displacing the intermediate carrier 2 in the direction parallel to the axis 6 (as in the embodiment according to FIGS. 2a and 2b), or by varying the focusing of the laser beam (as in the embodiment of FIGS. 3a and 3b). Optionally, it is also possible to shift the ion optical system 5 parallel to the axis 6 in the direction of arrow 21 to improve the acceptance during the second laser burst.

The housing 12 can consist of a tubular section 22. It is provided at the level of the sample support 17 and optionally at the level of the intermediate carrier support 13 with at least one transfer tube 23. By means of this transfer tube, it is possible to exchange samples and intermediate carriers without interrupting the vacuum to make, for example, additional analyses outside of the apparatus. The end face of housing 12 is sealed by means of a lid flange 24 having an observation window 25 for watching manipulations during changing of the samples.

It will be understood that the above description of the present invention is susceptible to various modifications, changes and adaptations, and the same are intended to be comprehended within the meaning and range of equivalents of the appended claims.

What is claimed is:

1. A method of analyzing a sample comprising the steps of:
   irradiating a selected area of said sample with a first burst of energy from a pulsed laser, said selected area being vaporized by the energy impinging thereon;
   condensing the vaporized sample material on the surface of an intermediate carrier; and
   analyzing the condensed sample material deposited on said intermediate carrier.

2. The method defined by claim 1 wherein said analyzing step includes irradiating the condensed sample material on said intermediate carrier with a second burst of energy from said pulsed laser to produce ions of said sample material.

3. The method defined by claim 2 which includes the step of determining the mass of said ions.

4. The method defined by claim 2 wherein a selected quantity of the sample material on said intermediate carrier is analyzed.

5. The method defined by claim 2 wherein all of the sample material on said intermediate carrier is analyzed.

6. The method defined by claim 2 wherein the sample material on said intermediate carrier is irradiated a plurality of times, and which includes the step of summing the mass spectra produced thereby.

7. The method defined by claims 2 or 6 wherein during said analyzing step a portion of said intermediate carrier is vaporized by said second burst of energy from said pulsed laser source, said vaporized portion of said intermediate carrier being used for calibration during analysis.

8. The method defined by claim 1 wherein said intermediate carrier is transparent to the energy from said pulsed laser.

9. The method defined by claims 2 or 6 wherein the energy from said pulsed laser is projected through a lens system and said analysis is carried out by means of a spectrometer, said method comprising the further steps of positioning said sample at an optimum distance from said lens system prior to irradiation by said sample with said first burst of laser energy, and positioning said intermediate carrier at an optimum distance from the inlet of said spectrometer following irradiation of said sample by said first burst of laser energy and prior to irradiation of said condensed sample on said intermediate carrier with said second burst of laser energy.

10. Apparatus for analyzing a sample, comprising
    an evacuatable housing,
    means for introducing brusts of laser energy into said housing,
    sample support means located within said housing for positioning said sample to receive a first burst of laser energy,
    an intermediate carrier located within said housing adjacent said sample support means for depositing thereon vapor produced by said first burst of laser energy, and
    means for recording the charged particles or quanta produced by a second burst of laser energy impinging on said intermediate carrier.

11. Apparatus as defined by claim 10 wherein said intermediate carrier comprises material which is transparent to said laser energy.

12. Apparatus as defined by claim 10 which further comprises movable intermediate carrier support means located within said housing for supporting a plurality of said intermediate carriers.

13. Apparatus as defined by claim 12 wherein said carrier support means is rotatable.

14. Apparatus as defined by claim 10 wherein said sample support means supports a plurality of samples and is moveable with respect to said housing.

15. Apparatus as defined by claim 14 wherein said sample support means is rotatable.

16. Apparatus as defined by claim 10 wherein said sample support means supports a plurality of samples on the periphery thereof, said sample support means being rotatable about an axis parallel to the axis of said housing and translatable in a direction normal to the axis of said housing; said apparatus further comprising intermediate carrier support means located within said housing for supporting a plurality of said intermediate carriers on the periphery thereof, said carrier support means being rotatable about an axis parallel to the axis of said housing and translatable in a direction parallel to the axis of said housing, said rotatable and translatable sample and intermediate carrier support means permitting said samples and intermediate carriers to be positioned prior to said first burst of laser energy for optimum vaporization and condensation of a desired area of said sample on an intermediate carrier and prior to said second burst of laser energy for optimum analysis of the sample material deposited on said intermediate carrier.

* * * * *